(12) United States Patent
Baek et al.

(10) Patent No.: US 10,217,653 B2
(45) Date of Patent: Feb. 26, 2019

(54) APPARATUS FOR TREATING SUBSTRATE

(71) Applicant: Samsung Electronics Co., Ltd., Suwon-si, Gyeonggi-do (KR)

(72) Inventors: Dongseok Baek, Suwon-si (KR); Jin Shin, Suwon-si (KR); Sungman Kim, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 269 days.

(21) Appl. No.: 15/094,072

(22) Filed: Apr. 8, 2016

(65) Prior Publication Data

US 2016/0343597 A1 Nov. 24, 2016

(30) Foreign Application Priority Data

May 22, 2015 (KR) .................. 10-2015-0071872

(51) Int. Cl.
| | |
|---|---|
| *H01L 21/67* | (2006.01) |
| *G01N 21/95* | (2006.01) |
| *G01N 21/94* | (2006.01) |
| *B24B 49/12* | (2006.01) |
| *H01L 21/68* | (2006.01) |

(52) U.S. Cl.
CPC ........ *H01L 21/67288* (2013.01); *B24B 49/12* (2013.01); *G01N 21/94* (2013.01); *G01N 21/9501* (2013.01); *H01L 21/67092* (2013.01); *H01L 21/67253* (2013.01); *H01L 21/681* (2013.01); *G01N 2201/0636* (2013.01)

(58) Field of Classification Search
CPC ......... H01L 21/67288; H01L 21/67092; H01L 21/681; B24B 49/12; G01N 21/9501
See application file for complete search history.

(56) References Cited

U.S. PATENT DOCUMENTS

| | | | |
|---|---|---|---|
| 6,609,962 B1 * | 8/2003 | Wakabayashi | B24B 1/04 451/443 |
| 7,102,743 B2 | 9/2006 | Tsuji et al. | |
| 8,697,542 B2 | 4/2014 | Pascual et al. | |
| 8,807,184 B2 | 8/2014 | Knickerbocker et al. | |
| 2001/0012392 A1 * | 8/2001 | Langley | H01L 21/67167 382/145 |

(Continued)

FOREIGN PATENT DOCUMENTS

| | | |
|---|---|---|
| KR | 2004-0005089 A | 1/2004 |
| KR | 10-0451988 B1 | 10/2004 |

(Continued)

*Primary Examiner* — Maurice Smith
(74) *Attorney, Agent, or Firm* — Harness, Dickey & Pierce, P.L.C.

(57) ABSTRACT

A substrate-treating apparatus according to an example embodiment of the inventive concepts includes a support unit on which a substrate is loaded, an optical measurement unit providing light to the substrate to obtain image data and checking whether the substrate is abnormal or not, based on the image data, and a control unit controlling the support unit and the optical measurement unit. The control unit processes the image data transmitted from the optical measurement unit. The control unit includes an interlock control part performing an interlock operation interrupting a process performed on the substrate if an abnormal signal is detected from the image data.

18 Claims, 21 Drawing Sheets

(56) References Cited

U.S. PATENT DOCUMENTS

| | | | |
|---|---|---|---|
| 2002/0154298 A1* | 10/2002 | Hagen | G01N 21/958 356/239.1 |
| 2003/0027494 A1* | 2/2003 | Yang | B23D 59/001 451/6 |
| 2005/0009450 A1* | 1/2005 | Finarov | B24B 37/345 451/6 |
| 2005/0130562 A1* | 6/2005 | Nabeya | B24B 37/005 451/6 |
| 2007/0032177 A1* | 2/2007 | Park | B24B 7/228 451/57 |
| 2013/0130424 A1 | 5/2013 | Horton et al. | |
| 2013/0218316 A1* | 8/2013 | Zhang | B24B 37/013 700/108 |
| 2014/0120802 A1* | 5/2014 | Duescher | B24B 37/005 451/6 |
| 2014/0295656 A1 | 10/2014 | Waterworth et al. | |
| 2015/0168303 A1* | 6/2015 | Trupke | G01N 21/6456 324/762.01 |

FOREIGN PATENT DOCUMENTS

| | | |
|---|---|---|
| KR | 2006-0103762 A | 10/2006 |
| KR | 2008-0053096 A | 6/2008 |
| KR | 2009-0058306 A | 6/2009 |
| KR | 10-1426841 B1 | 8/2014 |

* cited by examiner

APPARATUS FOR TREATING SUBSTRATE

CROSS-REFERENCE TO RELATED APPLICATION

This U.S. non-provisional patent application claims priority under 35 U.S.C. § 119 to Korean Patent Application No. 10-2015-0071872, filed on May 22, 2015, in the Korean Intellectual Property Office, the disclosure of which is hereby incorporated by reference in its entirety.

BACKGROUND

The inventive concepts relate to an apparatus for treating a substrate and, more particularly, to an apparatus for treating a substrate (hereinafter, referred to as 'a substrate-treating apparatus') capable of performing an interlock operation by optical measurement.

A substrate (e.g., a silicon wafer) may be generally coupled to a carrier supporting the substrate to thin the substrate by a back-lap process or a back grinding process during a semiconductor manufacturing process (e.g., a through silicon via (TSV) process, a high bandwidth memory (HBM) process, wafer support system (WSS) process, or a general packaging process). During the back grinding process, a back side of the wafer on which patterns are not formed may be grinded by a laser, chemical and/or mechanical polishing method. After the back grinding process, subsequent processes (e.g., a molding process and a sawing process) may be performed to complete a semiconductor package. At this time, if the subsequent processes are continuously performed in a state where a defect (e.g., a crack) occurs in the wafer, the wafer may be broken by pressure applied thereto. Thus, it may be necessary to verify a wafer having the defect (e.g., the crack) before the subsequent processes which are expensive and are performed for a long time.

SUMMARY

Example embodiments of the inventive concepts may provide a substrate-treating apparatus capable of measuring and monitoring defects (e.g., chippings or particles) of a substrate.

Example embodiments of the inventive concepts may also provide a substrate-treating apparatus capable of measuring and monitoring a blade unit provided to a substrate.

Example embodiments of the inventive concepts may also provide a substrate-treating apparatus capable of performing an interlock operation when an abnormal signal is sensed.

In one aspect, a substrate-treating apparatus may include a support unit on which a substrate is loaded, an optical measurement unit providing light to the substrate to obtain image data and checking whether the substrate is abnormal or not, based on the image data, and a control unit controlling the support unit and the optical measurement unit and processing the image data transmitted from the optical measurement unit. The control unit may include an interlock control part performing an interlock operation interrupting a process performed on the substrate if an abnormal signal is detected from the image data.

In an example embodiment, the optical measurement unit may include an optical member providing the light to the substrate, and a reflection member spaced apart from the optical member. The reflection member may reflect the light provided from the optical member to control a measurement range of the light.

In an example embodiment, the control unit may further include an image control part monitoring the image data received from the optical measurement unit. The image control may transmit the abnormal signal to the interlock control part when the abnormal signal is detected.

In an example embodiment, the optical measurement unit may further include a driving part moving the optical member.

In an example embodiment, the optical member may include a plurality of optical members.

In an example embodiment, the optical measurement unit may include a first optical member and a second optical member. The first optical member may check whether a central area of the substrate is abnormal or not, and the second optical member may check whether an edge area of the substrate is abnormal or not.

In an example embodiment, the reflection member of the optical measurement unit may include a first mirror opposite to the first optical member, and a second mirror opposite to the second optical member. The first mirror may be provided over the central area, and the second mirror may be provided over the edge area.

In an example embodiment, the control unit may rotate the support unit to rotate the substrate when the optical measurement unit checks whether the substrate is abnormal or not.

In an example embodiment, the substrate-treating apparatus may further include a blade unit provided at a side of the support unit and used to remove a layer provided on the substrate loaded on the support unit. The control unit may control the support unit, the optical measurement unit and the blade unit.

In an example embodiment, the optical measurement unit may further include a third optical member provided over the blade unit. The third optical member may check whether the blade unit is worn or not.

In an example embodiment, the optical measurement unit may further include a fourth optical member spaced apart from the blade unit when viewed from a plan view. The fourth optical member may detect a position of the blade unit when the blade unit approaches the layer of the substrate.

In an example embodiment, the control unit may perform an interlock operation interrupting operation of the blade unit, based on data obtained by any one of the third optical member and the fourth optical member.

In an example embodiment, the abnormal signal may include at least one of a signal corresponding to a chipping, a signal corresponding to a crack, a signal corresponding to a broken phenomenon, or a signal corresponding to a foreign substance.

In an example embodiment, the control unit may operate an alarm when the abnormal signal is detected.

In another example embodiment, a substrate-treating apparatus may include a support unit on which a substrate is loaded, a blade unit performing a process of treating the substrate, an optical measurement unit providing light to check at least one of a position of the blade unit or whether the substrate is abnormal or not, the optical measurement unit obtaining image data corresponding to the checked result, and a control unit controlling the support unit, the blade unit, and the optical measurement unit. The control unit may process the image data received from the optical measurement unit.

In an example embodiment, the control unit may perform an interlock operation interrupting the process when at least one of an abnormal signal of the substrate or an abnormal position signal of the blade unit is detected.

In an example embodiment, the process may include a process of removing a layer provided on the substrate, and the optical measurement unit may detect the position of the blade unit when the blade unit approaches the layer to remove the layer.

In an example embodiment, the optical measurement unit may include a first optical member and a second optical member. The first optical member may check whether a central area of the substrate is abnormal or not, and the second optical member may check whether an edge area of the substrate is abnormal or not.

In an example embodiment, the optical measurement unit may further include a third optical member and a fourth optical member. The third optical member may be disposed over the blade unit to check whether the blade unit is worn or not, and the fourth optical member may be spaced apart from the blade unit to detect the position of the blade unit.

In an example embodiment, the abnormal signal of the substrate may include at least one of a signal corresponding to a chipping, a signal corresponding to a crack, a signal corresponding to a broken phenomenon, or a signal corresponding to a foreign substance.

BRIEF DESCRIPTION OF THE DRAWINGS

The inventive concepts will become more apparent in view of the attached drawings and accompanying detailed description.

DETAILED DESCRIPTION OF EXAMPLE EMBODIMENTS

Figure 1:
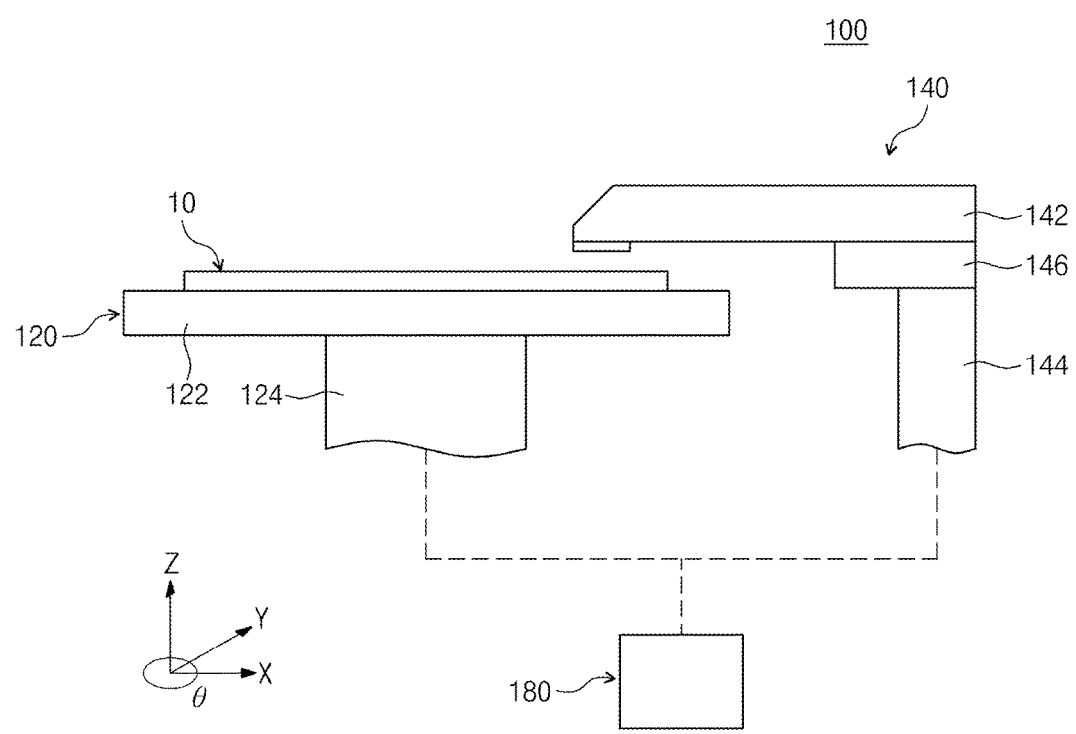
FIG. 1 is a schematic view illustrating a substrate-treating apparatus according to an example embodiment of the inventive concepts.

The inventive concepts will now be described more fully hereinafter with reference to the accompanying drawings, in which example embodiments of the inventive concepts are shown. The advantages and features of the inventive concepts and methods of achieving them will be apparent from the following example embodiments that will be described in more detail with reference to the accompanying drawings. It should be noted, however, that the inventive concepts are not limited to the following example embodiments, and may be implemented in various forms. Accordingly, the example embodiments are provided only to disclose the inventive concepts and let those skilled in the art know the category of the inventive concepts. In the drawings, example embodiments of the inventive concepts are not limited to the specific examples provided herein and are exaggerated for clarity. As used herein, the term "and/or" includes any and all combinations of one or more of the associated listed items. The same reference numerals or the same reference designators denote the same elements throughout the specification.

The terminology used herein is for the purpose of describing particular embodiments only and is not intended to limit the invention. As used herein, the singular terms "a," "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The example embodiments in the detailed description will be described with cross-sectional, perspective and plan views as ideal example views of the inventive concepts. In the drawings, the thicknesses of layers and regions are exaggerated for clarity. Accordingly, shapes of the example views may be modified according to manufacturing techniques and/or allowable errors.

The inventive concepts will now be described more fully hereinafter with reference to the accompanying drawings, in which example embodiments of the inventive concepts are shown. The advantages and features of the inventive concepts and methods of achieving them will be apparent from the following example embodiments that will be described in more detail with reference to the accompanying drawings. It should be noted, however, that the inventive concepts are not limited to the following example embodiments, and may be implemented in various forms. Accordingly, the example embodiments are provided only to disclose the inventive concepts and let those skilled in the art know the category of the inventive concepts. In the drawings, embodiments of the inventive concepts are not limited to the specific examples provided herein and are exaggerated for clarity.

The terminology used herein is for the purpose of describing particular embodiments only and is not intended to limit the invention. As used herein, the singular terms "a," "an" and "the" are intended to include the plural forms as well, unless the context clearly indicates otherwise. As used herein, the term "and/or" includes any and all combinations of one or more of the associated listed items. It will be understood that when an element is referred to as being "connected" or "coupled" to another element, it may be directly connected or coupled to the other element or intervening elements may be present.

Similarly, it will be understood that when an element such as a layer, region or substrate is referred to as being "on" another element, it can be directly on the other element or intervening elements may be present. In contrast, the term "directly" means that there are no intervening elements. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

Additionally, the embodiment in the detailed description will be described with sectional views as ideal example views of the inventive concepts. Accordingly, shapes of the example views may be modified according to manufacturing techniques and/or allowable errors. Therefore, the embodiments of the inventive concepts are not limited to the specific shape illustrated in the example views, but may include other shapes that may be created according to manufacturing processes. Areas exemplified in the drawings have general properties, and are used to illustrate specific shapes of elements. Thus, this should not be construed as limited to the scope of the inventive concepts.

It will be also understood that although the terms first, second, third etc. may be used herein to describe various elements, these elements should not be limited by these terms. These terms are only used to distinguish one element from another element. Thus, a first element in some embodiments could be termed a second element in other embodiments without departing from the teachings of the present invention. Exemplary embodiments of aspects of the present inventive concepts explained and illustrated herein include their complementary counterparts. The same reference numerals or the same reference designators denote the same elements throughout the specification.

Moreover, example embodiments are described herein with reference to cross-sectional illustrations and/or plane illustrations that are idealized example illustrations. Accordingly, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing. For example, an etching region illustrated as a rectangle will, typically, have rounded or curved features. Thus, the regions illustrated in the figures are schematic in nature and their shapes are not intended to illustrate the actual shape of a region of a device and are not intended to limit the scope of example embodiments.

As appreciated by the present inventive entity, devices and methods of forming devices according to various embodiments described herein may be embodied in microelectronic devices such as integrated circuits, wherein a plurality of devices according to various embodiments described herein are integrated in the same microelectronic device. Accordingly, the cross-sectional view(s) illustrated herein may be replicated in two different directions, which need not be orthogonal, in the microelectronic device. Thus, a plan view of the microelectronic device that embodies devices according to various embodiments described herein may include a plurality of the devices in an array and/or in a two-dimensional pattern that is based on the functionality of the microelectronic device.

The devices according to various embodiments described herein may be interspersed among other devices depending on the functionality of the microelectronic device. Moreover, microelectronic devices according to various embodiments described herein may be replicated in a third direction that may be orthogonal to the two different directions, to provide three-dimensional integrated circuits.

Accordingly, the cross-sectional view(s) illustrated herein provide support for a plurality of devices according to various embodiments described herein that extend along two different directions in a plan view and/or in three different directions in a perspective view. For example, when a single active region is illustrated in a cross-sectional view of a device/structure, the device/structure may include a plurality of active regions and transistor structures (or memory cell structures, gate structures, etc., as appropriate to the case) thereon, as would be illustrated by a plan view of the device/structure.

Figure 2:
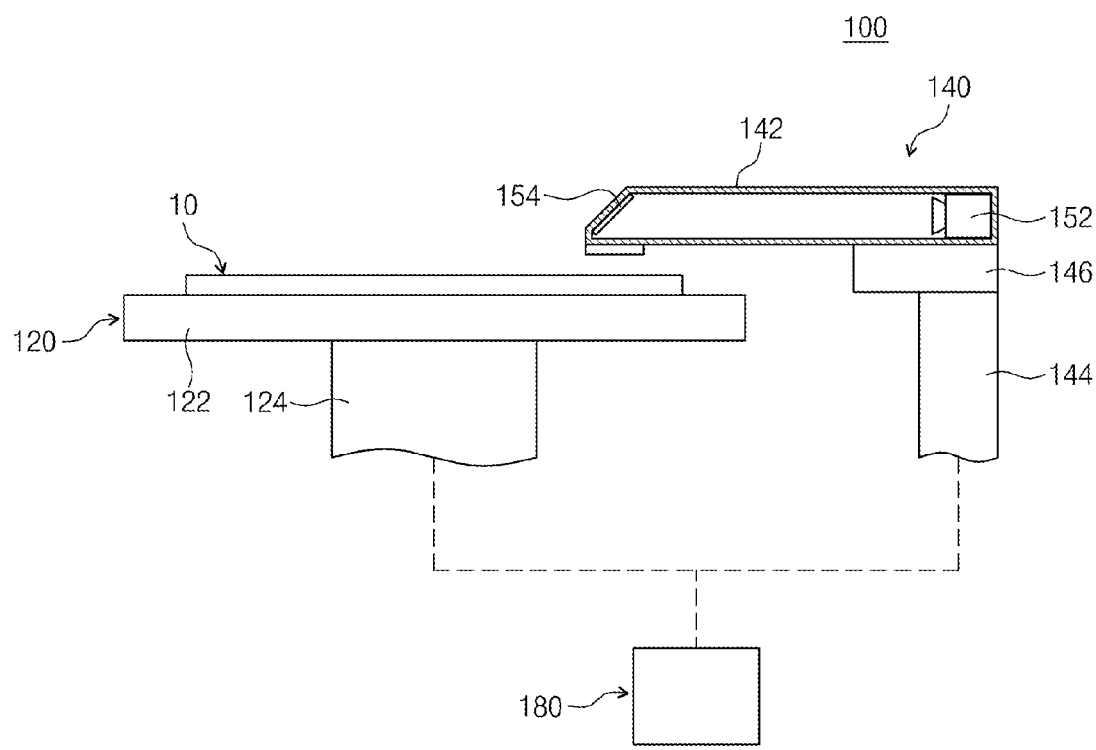
FIG. 2 is a cross-sectional view illustrating an optical measurement unit of FIG. 1.
Figure 3:
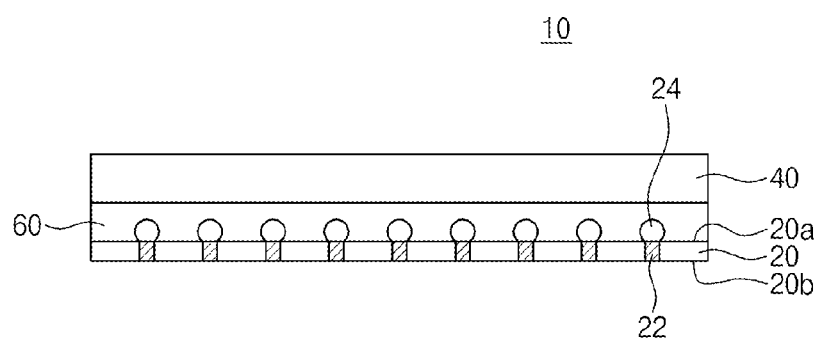
FIG. 3 is a cross-sectional view schematically illustrating a substrate according to an example embodiment of the inventive concepts.

FIG. 1 is a schematic view illustrating a substrate-treating apparatus 100 according to an example embodiment of the inventive concepts, and FIG. 2 is a cross-sectional view illustrating an optical measurement unit 140 of FIG. 1. FIG. 3 is a cross-sectional view schematically illustrating a substrate 10 according to an example embodiment of the inventive concepts.

Referring to FIGS. 1 to 3, the substrate-treating apparatus 100 may include a support unit 120, an optical measurement unit 140, and a control unit 180. A substrate 10 may be loaded on the support unit 120. The substrate 10 may be a semiconductor substrate. In an example embodiment, as illustrated in FIG. 3, the substrate 10 may include a device wafer 20, a carrier wafer 40, and an adhesive layer 60. The device wafer 20 may have a top surface 20a on which an integrated circuit (not shown) is formed, and a bottom surface 20b opposite to the top surface 20a. The integrated circuit (not shown) may include a memory circuit, a logic circuit, or a combination thereof. The device wafer 20 may include a plurality of through electrodes 22, and a plurality of bumps 24 disposed on the top surface 20a of the device wafer 20 so as to be electrically connected to the through electrodes 22. The device wafer 20 may be thin. For example, the thickness of the device wafer 20 may be in a range of 50 μm to 200 μm. The carrier wafer 40 may support the device wafer 20. The carrier wafer 40 may have the same size and shape as the device wafer 20. However, the size and shape of the carrier wafer 40 are not limited thereto. The carrier wafer 40 may include a quartz substrate, a glass substrate, a semiconductor substrate, a ceramic substrate, or a metal substrate. The device wafer 20 may be bonded to the carrier wafer 40 having mechanical strength, so the device wafer 20 may be easily handled. The adhesive layer 60 may couple the device wafer 20 to the carrier wafer 40. The adhesive layer 60 may include a material including silicon or a thermosetting resin including silicon. Alternatively, the adhesive layer 60 may include a material having various compositions.

The support unit 120 may include a support plate 122 and a support shaft 124. The substrate 10 may be loaded on a top surface of the support plate 122. For example, the support plate 122 may support the substrate 10 by means of a vacuum. Alternatively, the support plate 122 may support the substrate by means of electrostatic force. The support shaft 124 may support and rotate the support plate 122. In an example embodiment, the support shaft 124 may receive rotatory power from a driving unit (not shown) to rotate the support plate 122. The driving unit (not shown) may be a motor.

The optical measurement unit 140 may be disposed along a side of the support unit 120. The optical measurement unit 140 may include a housing 142, a shaft 144, and a driving part 146. The housing 142 may include an optical member 152 and a reflection member 154. The optical measurement unit 140 may provide light to the substrate 10 to obtain image data and may check or determine whether the substrate 10 is abnormal or not, based on the obtained image data. The optical member 152 may provide the light to the substrate 10 to obtain the image data. For example, the optical member 152 may be a camera. The reflection member 154 may be spaced apart from the optical member 152. In an example embodiment, the optical member 152 and the reflection member 154 may be disposed at one end and another end of the housing 142, respectively. The reflection member 154 may reflect the light incident from the optical member 152 to control an optical measurement range. The reflection member 154 may be a mirror. The shaft 144 may support the optical member 152. In an example embodiment, the shaft 144 may control a height of the optical member 152. The driving part 146 may move the optical member 152. The driving part 146 may move the optical member 152 in an x-axis direction, a y-axis direction perpendicular to the x-axis direction, and a z-axis direction perpendicular to the x-axis and y-axis directions. In addition, the driving part 146 may control a rotation angle θ. In an example embodiment, the optical member 152 may not be disposed in the housing 142, and the driving part 146 and the shaft 144 may be coupled directly to the optical member 152. Hereinafter, the optical member 152 and the reflection member 154 which are elements independent of the housing 152 will be described as an example.

Figure 4:
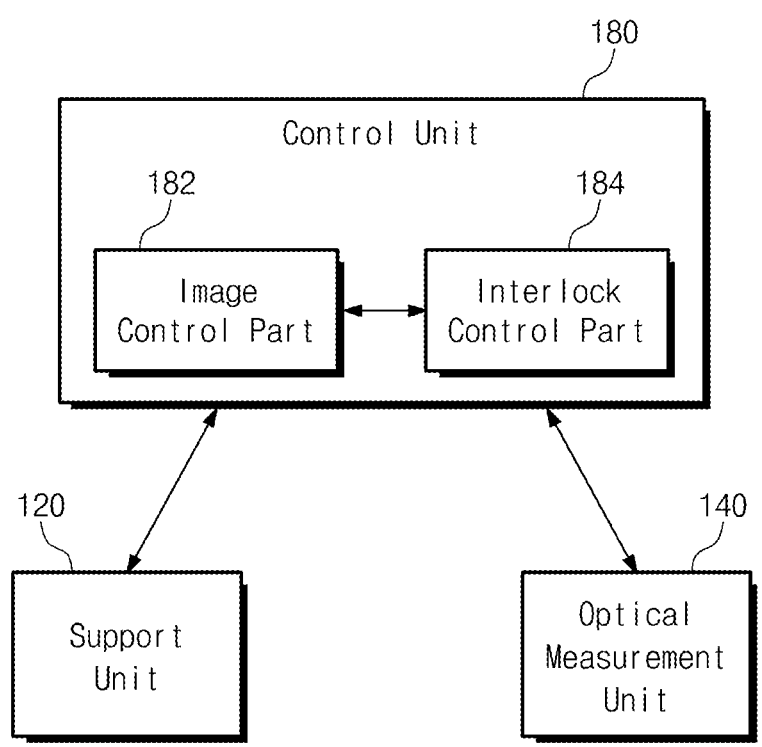
FIG. 4 is a schematic block diagram illustrating a control unit of FIGS. 1 and 2.

FIG. 4 is a schematic block diagram illustrating the control unit 180 of FIGS. 1 and 2. The control unit 180 may control the support unit 120 and the optical measurement unit 140. The control unit 180 may process the image data transmitted from the optical measurement unit 140. Referring to FIG. 4, the control unit 180 may include an image control part 182 and an interlock control part 184. The image control part 182 may display the image data transmitted from the optical measurement unit 140. For example, the image control part 182 may be a personal computer (PC). The image control part 182 may display the image data, so a worker may monitor the image data in real time. If an abnormal signal is detected from the image data, the image control part 182 may transmit the abnormal signal to the interlock control part 184. If the abnormal signal is detected, the interlock control part 184 may perform an interlock operation interrupting a process performed on the substrate 10. In addition, if the abnormal signal is detected, the control unit 180 may operate an alarm. For example, the abnormal signal may include at least one of a signal corresponding to a chipping, a signal corresponding to a crack, a signal corresponding to a broken phenomenon, or a signal corresponding to a foreign substance.

Figure 5:
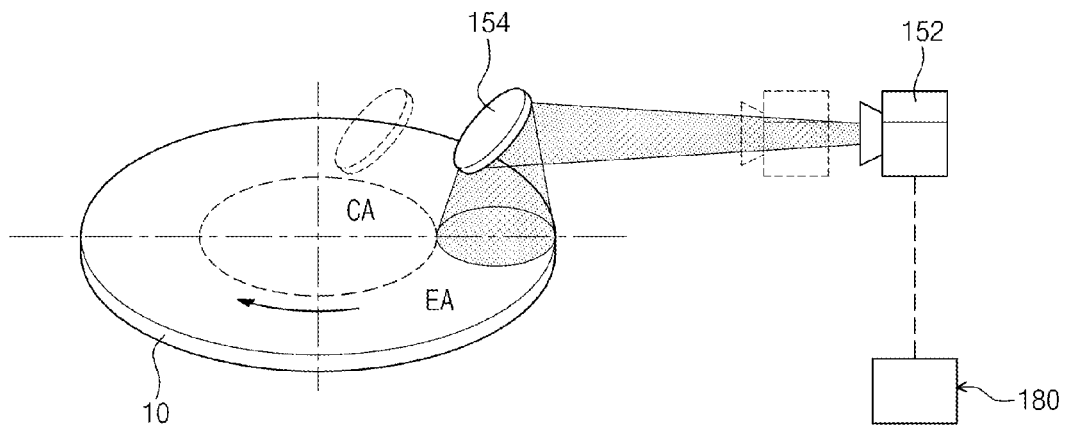
FIGS. 5 and 6 are views illustrating a method of obtaining image data from a substrate by means of the substrate-treating apparatus of FIG. 1.
Figure 6:
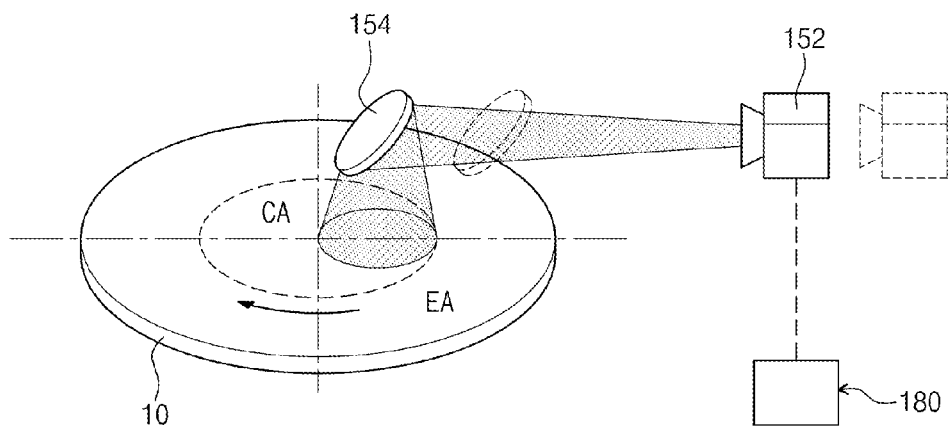

FIGS. 5 and 6 are views illustrating a method of obtaining image data from the substrate 10 the substrate-treating apparatus 100 of FIGS. 1 and 2. Referring to FIGS. 5 and 6, the substrate 10 may include a central area CA and an edge area EA. When the optical member 152 checks whether the edge area EA is abnormal or not, the control unit 180 may control a position of the optical measurement unit 140 such that the reflection member 154 is disposed over the edge area EA. At this time, the control unit 180 may control the support unit 120 to rotate the substrate 10. In addition, the control unit 180 may control the optical measurement unit 140 such that the optical member 152 and the reflection member 154 check whether the central area CA is abnormal or not. For example, the control unit 180 may control the driving part 146 such that the reflection member 154 is moved to be disposed over the central area CA. At this time, the control unit 180 may control the driving part 146 in such a way that the optical member 152 and the reflection member 154 are moved along a radial direction of the substrate 10. The control unit 180 may control the support unit 120 to rotate the substrate 10. Thus, checking whether abnormality occurs or not may be performed on an entire area of the substrate 100.

Figure 7:
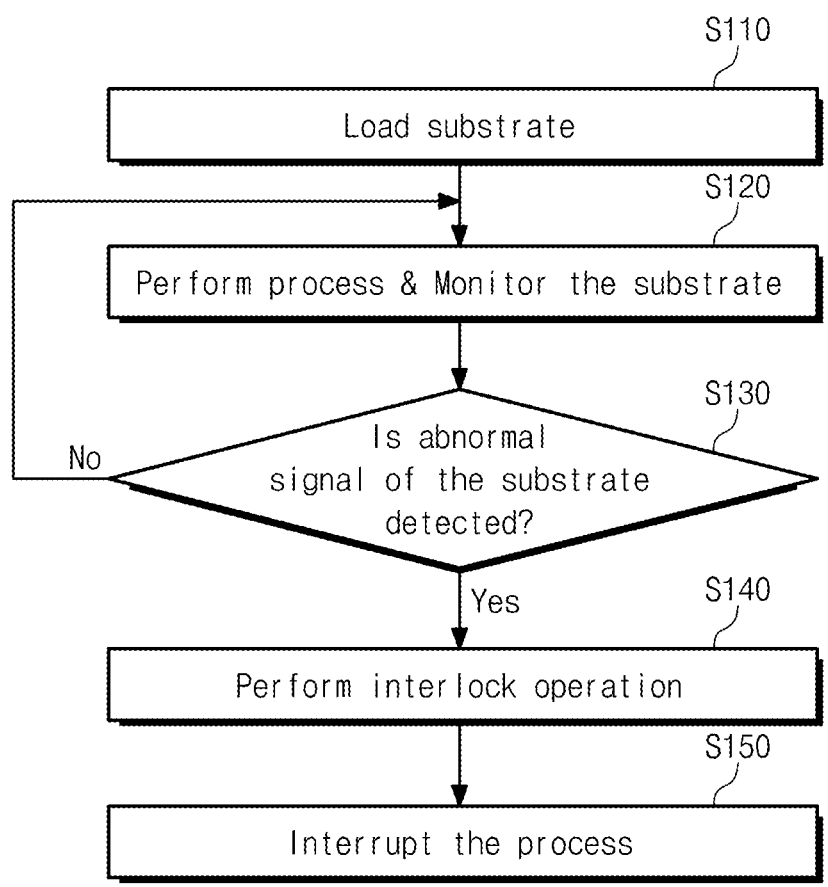
FIG. 7 is a flow chart illustrating a method of performing an interlock operation by means of the substrate-treating apparatus of FIG. 1.

FIG. 7 is a flow chart illustrating a method of performing an interlock operation by the substrate-treating apparatus 100 of FIGS. 1 and 2. A substrate 10 may be loaded on the support unit 120 (S110). The substrate 10 may be a package substrate. Alternatively, the substrate 10 may be a glass substrate. Thereafter, a process may be performed on the substrate 10, and the optical measurement unit 140 may monitor the substrate 10 (S120). The control unit 180 may analyze image data transmitted from the optical measurement unit 140 to determine whether an abnormal signal of the substrate 10 is detected or not (S130). If the abnormal signal is detected, the control unit 180 may perform an interlock operation to interrupt the process (S140 and S150). At this time, the control unit 180 may operate an alarm. For example, the abnormal signal may include at least one of a signal corresponding to a chipping, a signal corresponding to a crack, a signal corresponding to a broken phenomenon, or a signal corresponding to a foreign substance. If the abnormal signal is not detected, the process may be continuously performed on the substrate 10. In an example embodiment, the process may be a de-bonding process for separating the device wafer 20 from the carrier wafer 40.

Figure 8:
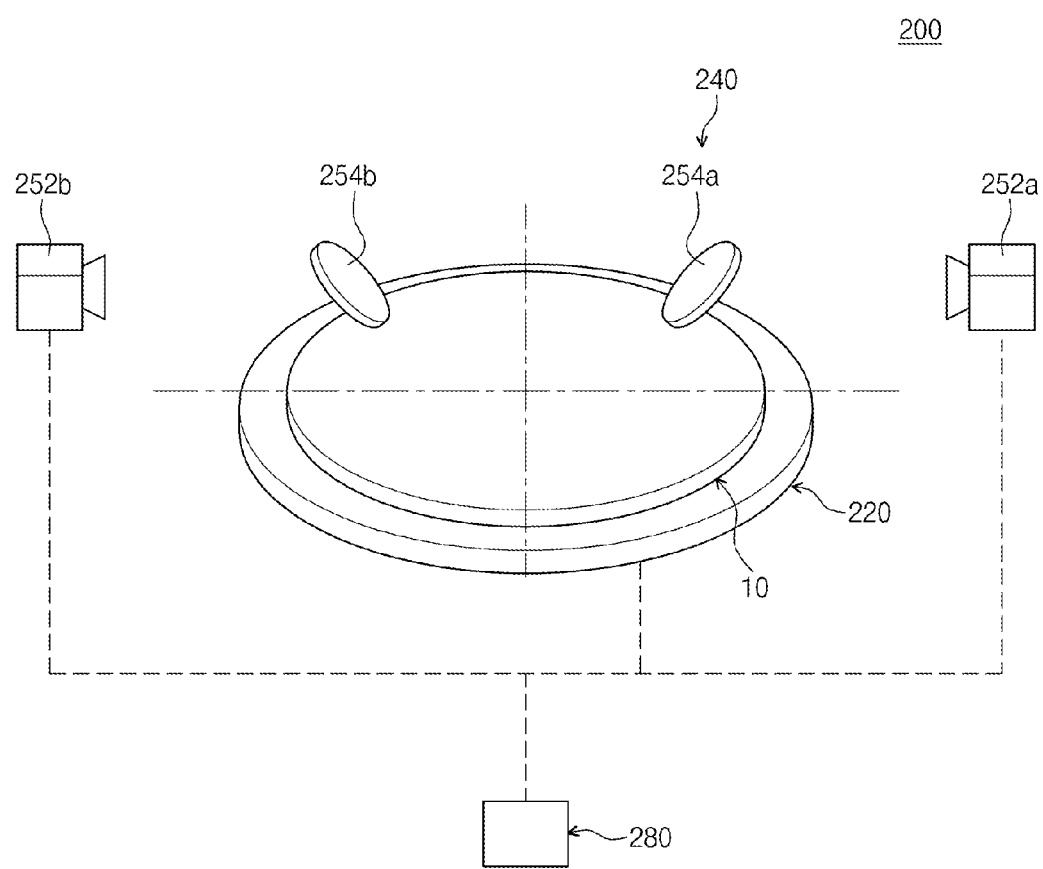
FIG. 8 is a schematic view illustrating a substrate-treating apparatus according to an example embodiment of the inventive concepts.
Figure 9:
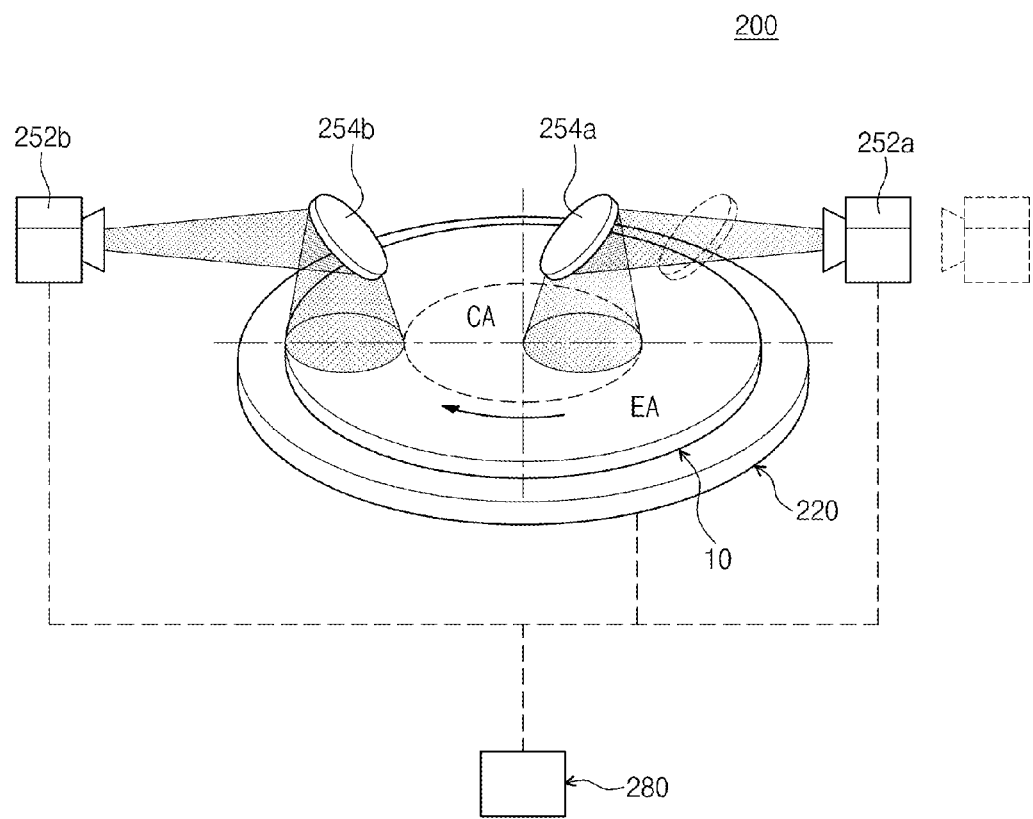
FIG. 9 is a schematic view illustrating optical measurement using the substrate-treating apparatus of FIG. 8.

FIG. 8 is a schematic view illustrating a substrate-treating apparatus 200 according to an example embodiment of the inventive concepts. FIG. 9 is a schematic view illustrating optical measurement using the substrate-treating apparatus 200 of FIG. 8.

Referring to FIGS. 8 and 9, the substrate-treating apparatus 200 may include a support unit 220, an optical measurement unit 240, and a control unit 280. The support unit 220 and the control unit 280 of the substrate-treating apparatus 200 of FIG. 8 may have the same or similar shapes and functions as the support unit 120 and the control unit 180 of the substrate-treating apparatus 100 of FIG. 1, respectively, and thus their descriptions will be omitted for the purpose of ease and convenience in explanation. However, the substrate-treating apparatus 200 of FIG. 8 may include a plurality of optical members 252a and 252b and a plurality of reflection members 254a and 254b. For example, the optical members 252a and 252b may include a first optical member 252a and a second optical member 252b, and the reflection members 254a and 254b may include a first mirror 254a and a second mirror 254b. The two optical members 252a and 252b may be disposed to be opposite to each other over the substrate 10, and the two reflection members 254a and 254b may also be disposed to be opposite to each other over the substrate 10. Referring to FIG. 9, when abnormality of the substrate 10 is optically measured, the first optical member 252a and the first mirror 254a may check whether the central area CA is abnormal or not, and the second optical member 252b and the second mirror 254b may check whether the edge area EA is abnormal or not. At this time, the first mirror 254a may be disposed over the central area CA of the substrate 10, and the second mirror 254b may be disposed over the edge area EA of the substrate 10. At this time, the control unit 280 may rotate the support unit 220 to rotate the substrate 10. Thus, an entire area of the substrate 10 may be checked during one revolution of the substrate 10. The control unit 280 may analyze image data transmitted from the optical measurement unit 240 to determine whether an abnormal signal of the substrate 10 occurs or not. If the abnormal signal is detected, the control unit 280 may perform the interlock operation to interrupt a process. At this time, the control unit 280 may operate an alarm. For example, the abnormal signal may include at least one of signals corresponding to a chipping, a crack, a broken phenomenon, and a foreign substance. If the abnormal signal is not detected, the process may be continuously performed on the substrate 10. In an example embodiment, the process may be a de-bonding process for separating the device wafer 20 from the carrier wafer 40.

Figure 10:
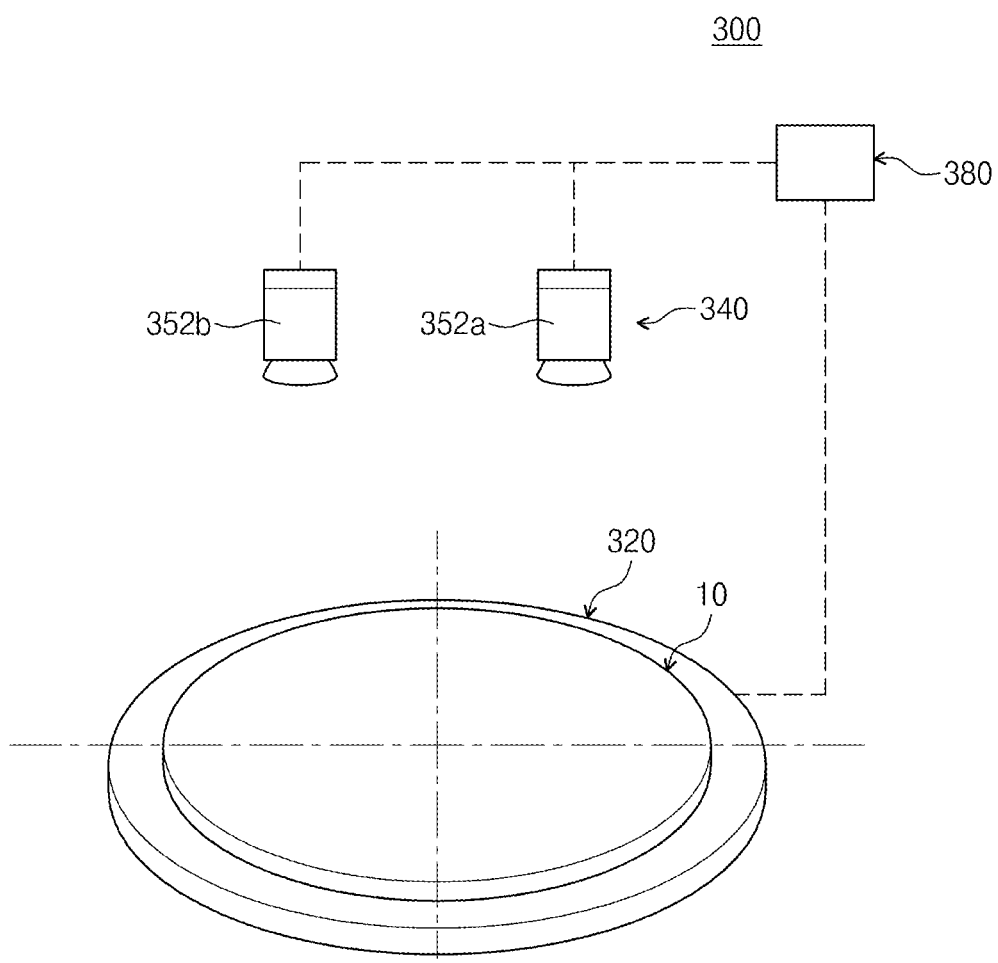
FIG. 10 is a schematic view illustrating a substrate-treating apparatus according to an example embodiment of the inventive concepts.
Figure 11:
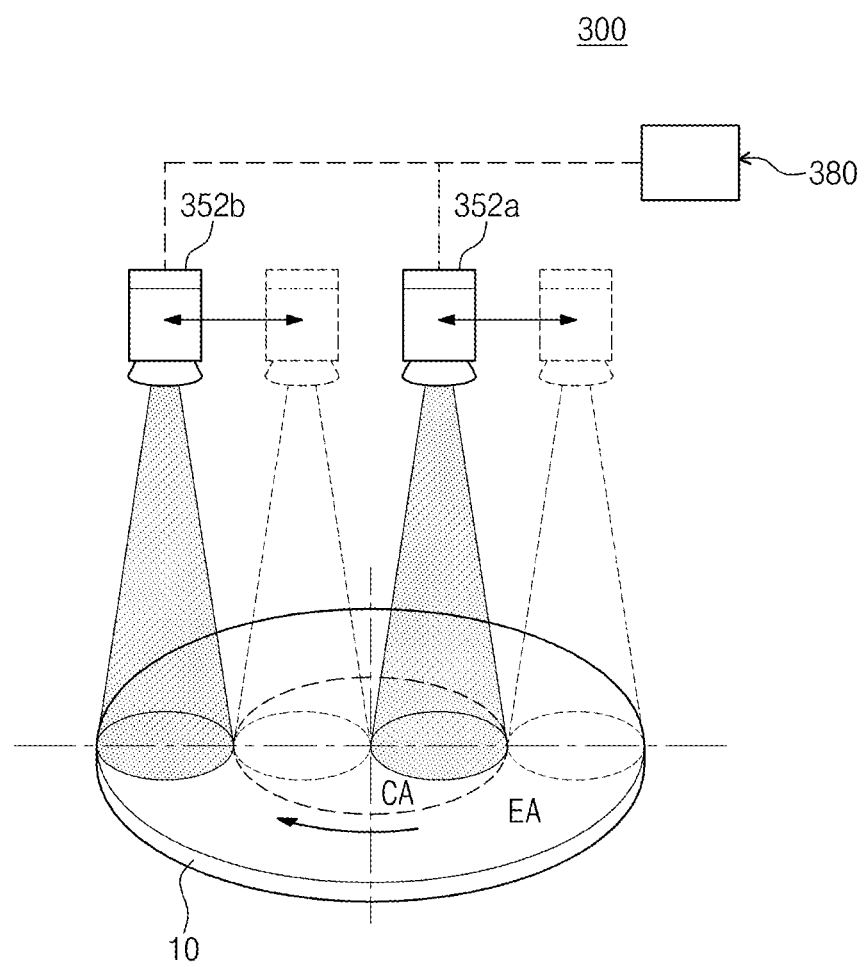
FIG. 11 is a schematic view illustrating optical measurement using the substrate-treating apparatus of FIG. 10.

FIG. 10 is a schematic view illustrating a substrate-treating apparatus 300 according to an example embodiment of the inventive concepts. FIG. 11 is a schematic view illustrating optical measurement using the substrate-treating apparatus 300 of FIG. 10.

Referring to FIGS. 10 and 11, the substrate-treating apparatus 300 may include a support unit 320, an optical measurement unit 340, and a control unit 380. The support unit 320 and the control unit 380 of the substrate-treating apparatus 300 of FIG. 10 may have the same or similar shapes and functions as the support unit 120 and the control unit 180 of the substrate-treating apparatus 100 of FIG. 1, respectively, and thus their descriptions will be omitted for the purpose of ease and convenience in explanation. However, the substrate-treating apparatus 300 of FIG. 10 may include a plurality of optical members 352a and 352b but may not include a reflection member. For example, the optical members 352a and 352b may include a first optical member 352a and a second optical member 352b. Since the substrate-treating apparatus 300 does not include the reflection member, the plurality of optical members 352a and 352b may directly provide light to the substrate 10. Referring to FIG. 11, when abnormality of the substrate 10 is optically measured, the first optical member 352a may check whether the central area CA is abnormal or not, and the second optical member 352b may check whether the edge area EA is abnormal or not. At this time, the first optical member 352a may be disposed over the central area CA of the substrate 10, and the second optical member 352b may be disposed over the edge area EA of the substrate 10. At this time, the control unit 380 may rotate the support unit 320 to rotate the substrate 10. The control unit 380 may rotate the substrate 10 and, at the same time, may linearly move the first and second optical members 352a and 352b over the substrate 100. In an example embodiment, the control unit 380 may perform the optical measurement while linearly reciprocating the first and second optical members 352a and 352b over the substrate 10. At this time, the control unit 380 may reciprocate the first and second optical members 352a and 352b along a radial direction at the same speed. Thus, an entire area of the substrate 10 may be detected during one revolution of the substrate 10. The control unit 380 may analyze image data transmitted from the optical measurement unit 340 to determine whether an abnormal signal of the substrate 10 occurs or not. If the abnormal signal is detected, the control unit 380 may perform the interlock operation to interrupt a process. At this time, the control unit 380 may operate an alarm. For example, the abnormal signal may include at least one of signals corresponding to a chipping, a crack, a broken phenomenon, and a foreign substance. If the abnormal signal is not detected, the process may be continuously performed on the substrate 10. In an example embodiment, the process may be a de-bonding process for separating the device wafer 20 from the carrier wafer 40.

Figure 12:
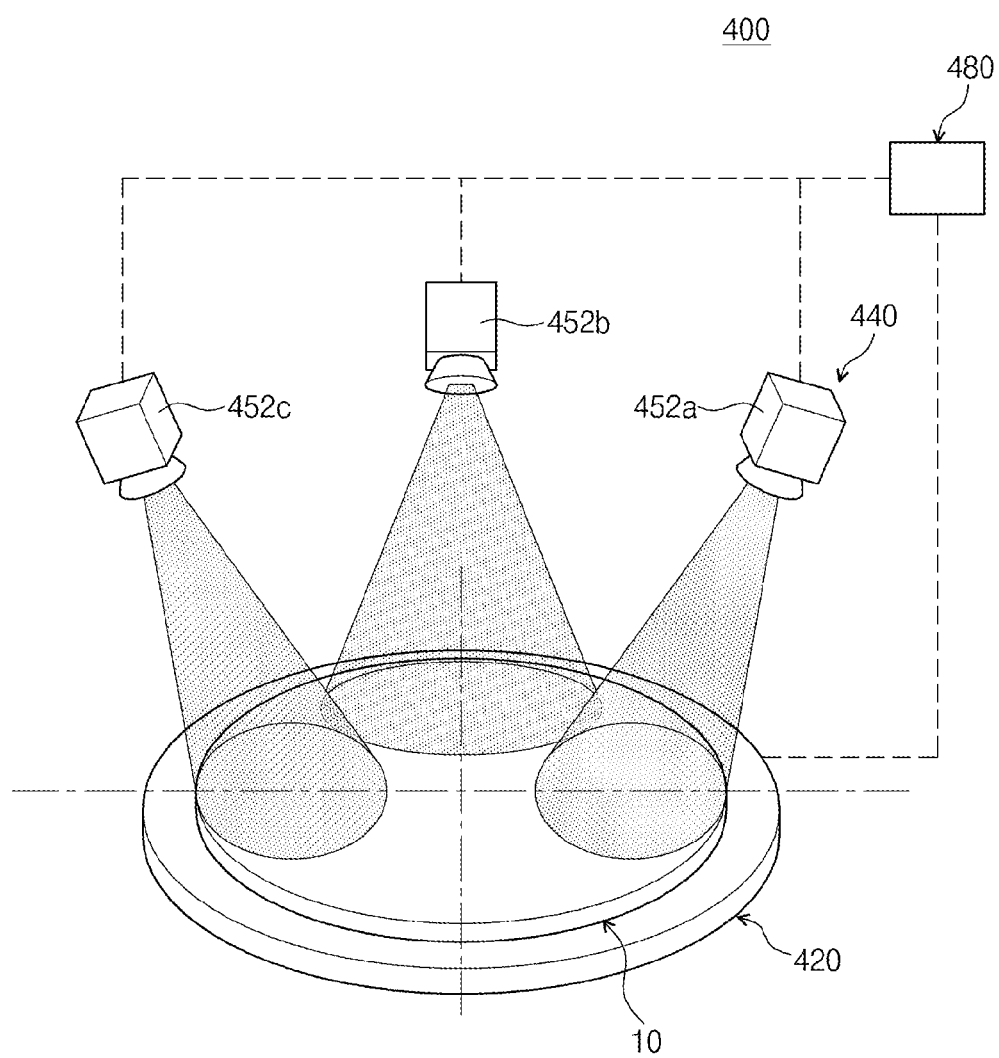
FIG. 12 is a schematic view illustrating a substrate-treating apparatus according to an example embodiment of the inventive concepts.
Figure 13:
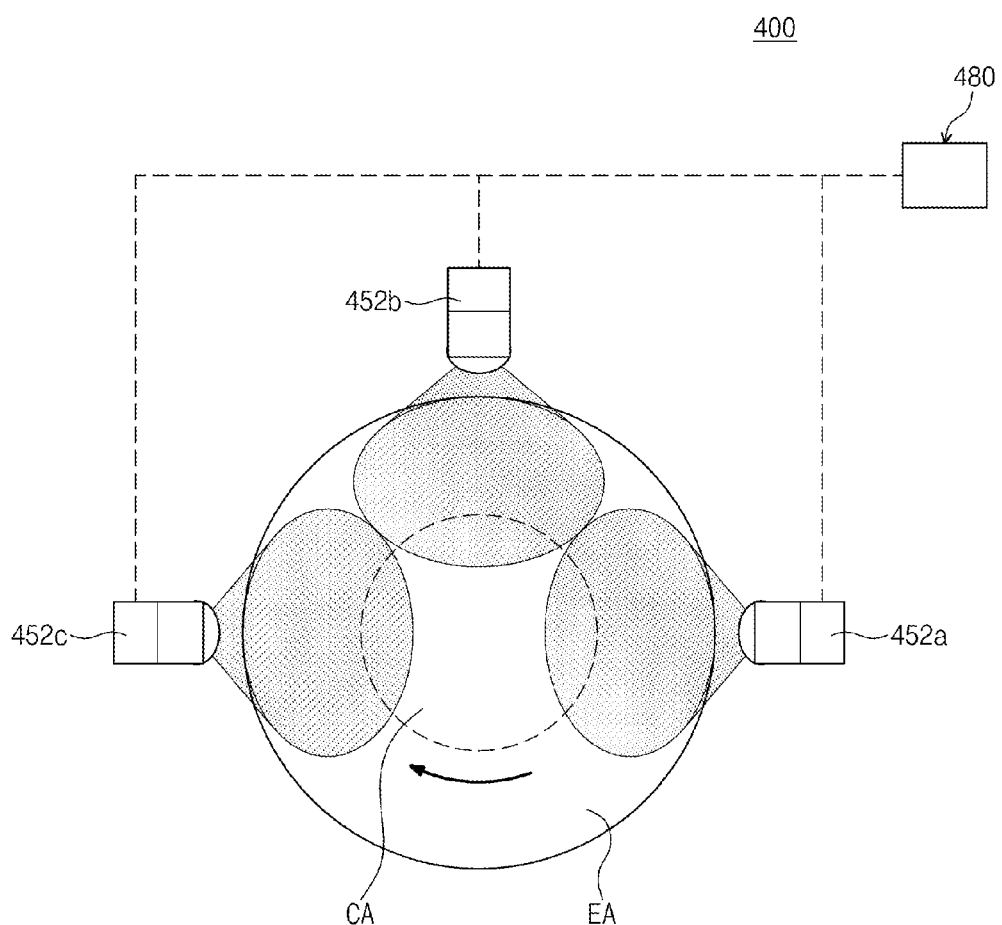
FIG. 13 is a schematic view illustrating optical measurement using the substrate-treating apparatus of FIG. 12.

FIG. 12 is a schematic view illustrating a substrate-treating apparatus 400 according to an example embodiment of the inventive concepts. FIG. 13 is a schematic view illustrating optical measurement using the substrate-treating apparatus 400 of FIG. 12.

Referring to FIGS. 12 and 13, the substrate-treating apparatus 400 may include a support unit 420, an optical measurement unit 440, and a control unit 480. The support unit 420 and the control unit 480 of the substrate-treating apparatus 400 of FIG. 12 may have the same or similar shapes and functions as the support unit 120 and the control unit 180 of the substrate-treating apparatus 100 of FIG. 1, respectively, and thus their descriptions will be omitted for the purpose of ease and convenience in explanation. However, the substrate-treating apparatus 400 of FIG. 12 may include a plurality of optical members 452a, 452b and 452c but may not include a reflection member. For example, the optical members 452a, 452b and 452c may include a first optical member 452a, a second optical member 452b, and a third optical member 452c. Since the substrate-treating apparatus 400 does not include the reflection member, the plurality of optical members 452a, 452b and 452c may directly provide light to the substrate 10. The plurality of optical members 452a, 452b and 452c may not move over the substrate 10 but may be fixed over the substrate 10. Referring to FIG. 13, when abnormality of the substrate 10 is optically measured, the plurality of optical members 452a, 452b and 452c may check whether the edge area EA of the substrate 10 is abnormal or not. Since a generation rate of a chipping or a foreign substance of the edge area EA is higher than that of the central area CA, the plurality of optical members 452a, 452b and 452c may check only the edge area EA of the substrate 10. At this time, the control unit 480 may rotate the support unit 420 to rotate the substrate 10. Thus, an entire area of the substrate 10 may be detected during one revolution of the substrate 10. The control unit 480 may analyze image data transmitted from the optical measurement unit 440 to determine whether an abnormal signal of the substrate 10 occurs or not. If the abnormal signal is detected, the control unit 480 may perform the interlock operation to interrupt a process. At this time, the control unit 480 may operate an alarm. For example, the abnormal signal may include at least one of signals corresponding to a chipping, a crack, a broken phenomenon, and a foreign substance. If the abnormal signal is not detected, the process may be continuously performed on the substrate 10. In an example embodiment, the process may be a de-bonding process for separating the device wafer 20 from the carrier wafer 40.

Figure 14:
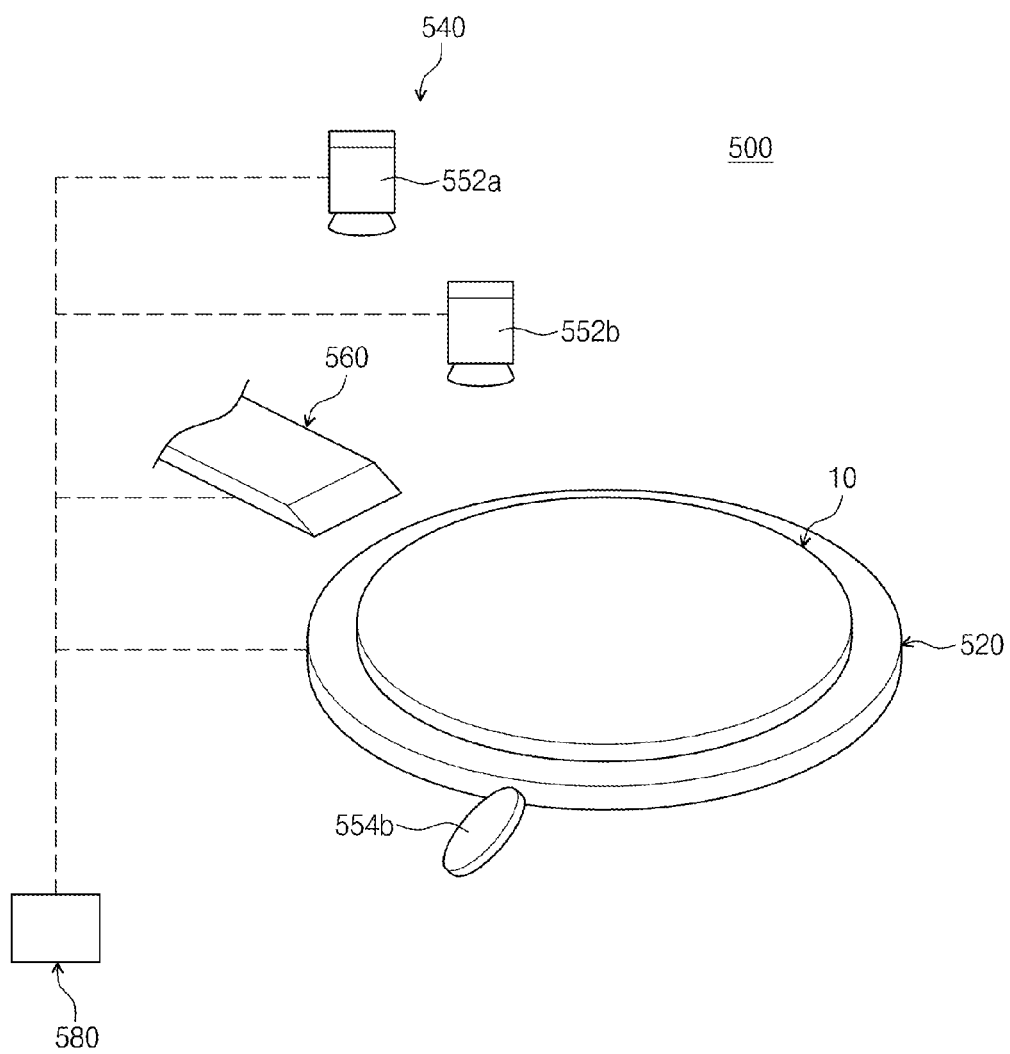
FIG. 14 is a schematic view illustrating a substrate-treating apparatus according to an example embodiment of the inventive concepts.
Figure 15:
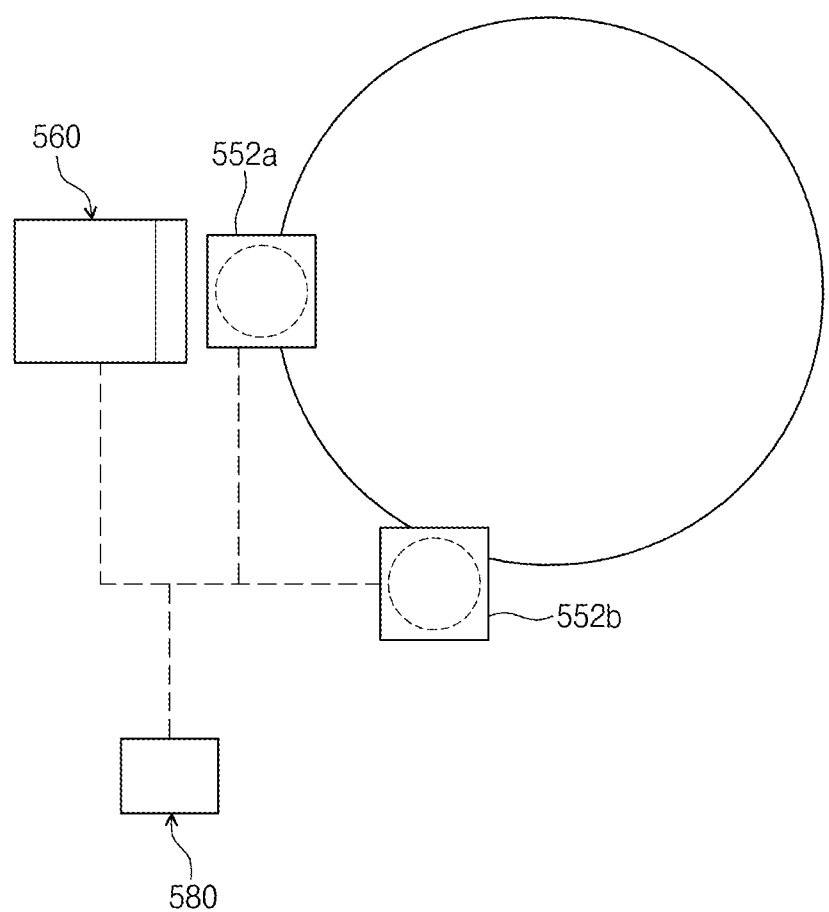
FIG. 15 is a plan view illustrating the substrate-treating apparatus of FIG. 14.
Figure 16:
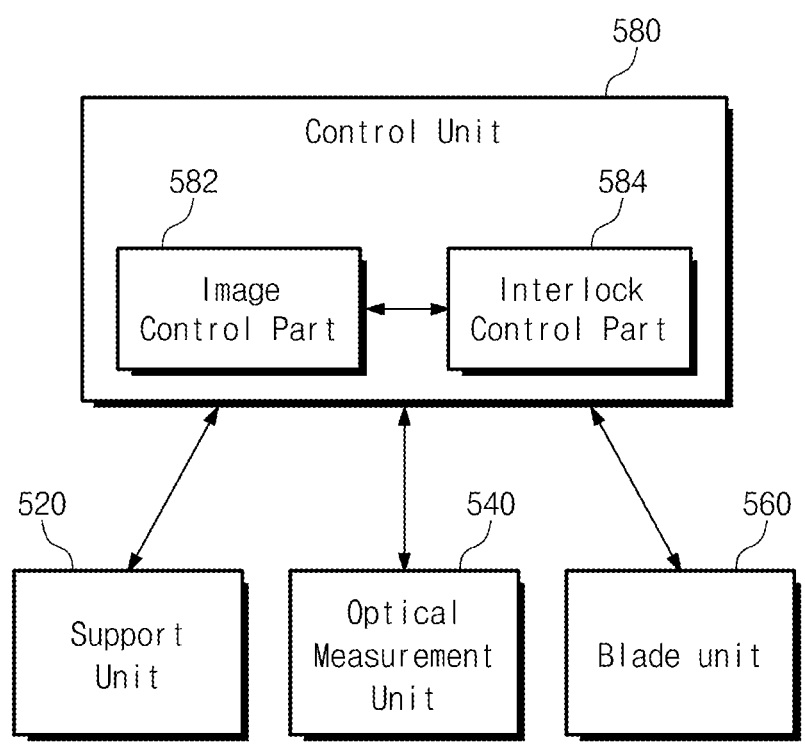
FIG. 16 is a schematic block diagram illustrating a control unit of FIG. 14.
Figure 17:
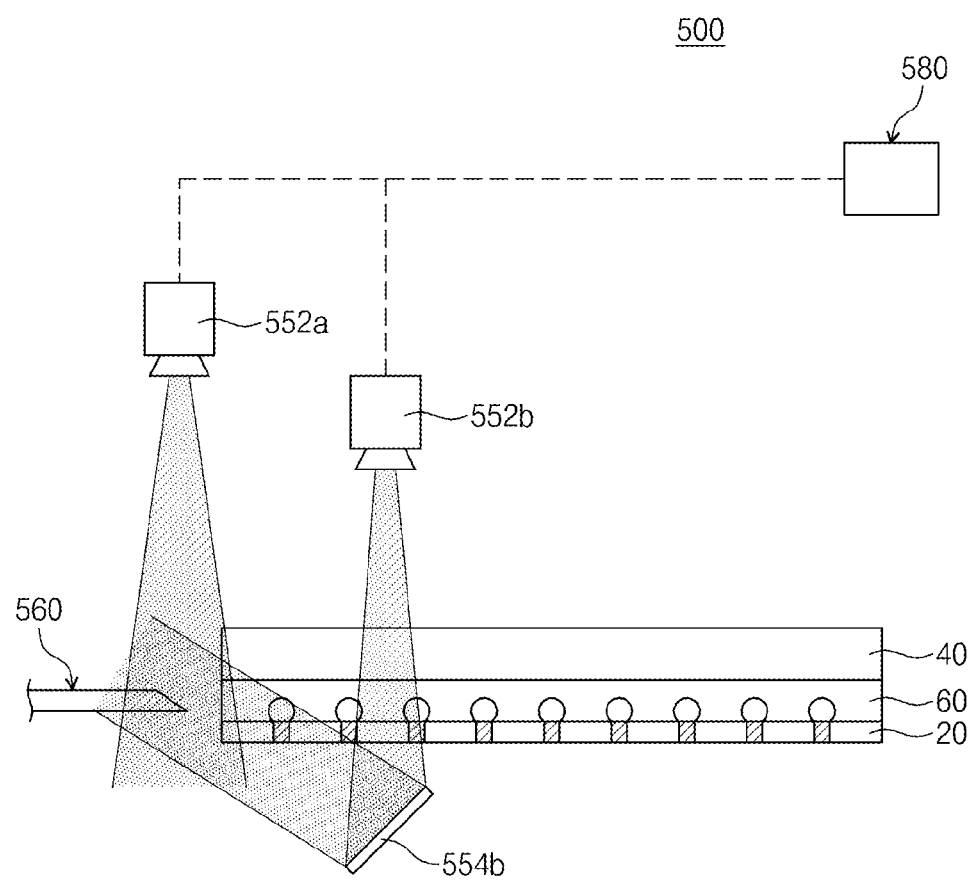
FIGS. 17 and 20 are schematic views illustrating optical measurement using the substrate-treating apparatus of FIG. 14.
Figure 18:
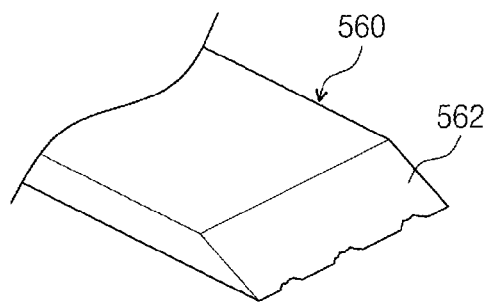
FIG. 18 is a schematic view illustrating optical measurement using a first optical member of FIG. 14.
Figure 19:
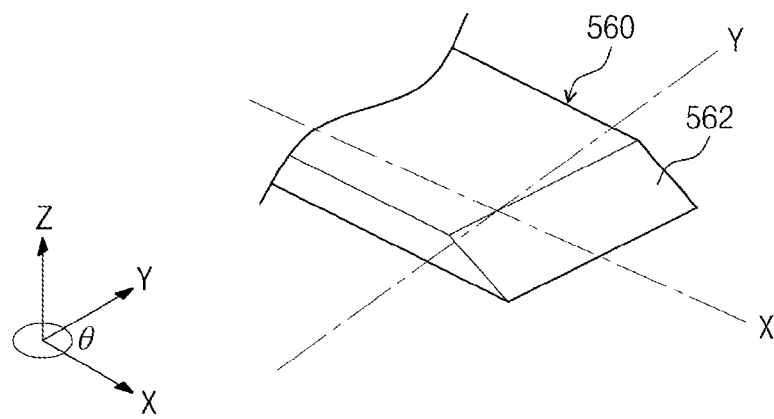
FIG. 19 is a schematic view illustrating optical measurement using a second optical member of FIG. 14.
Figure 20:
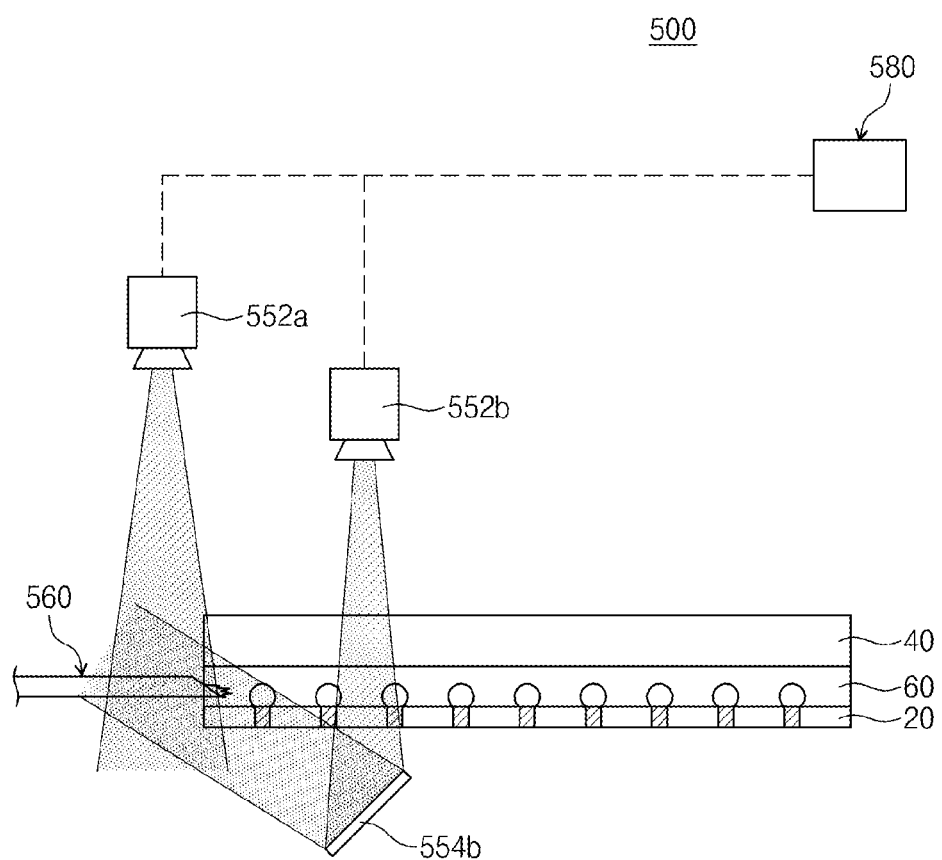

FIG. 14 is a schematic view illustrating a substrate-treating apparatus 500 according to an example embodiment of the inventive concepts. FIG. 15 is a plan view illustrating the substrate-treating apparatus 500 of FIG. 14. FIG. 16 is a schematic block diagram illustrating a control unit 580 of FIG. 14. FIGS. 17 and 20 are schematic views illustrating optical measurement using the substrate-treating apparatus 500 of FIG. 14. FIG. 18 is a schematic view illustrating optical measurement using a first optical member 552a of FIG. 14, and FIG. 19 is a schematic view illustrating optical measurement using a second optical member 552b of FIG. 14.

Referring to FIGS. 14 and 15, the substrate-treating apparatus 500 may include a support unit 520, an optical measurement unit 540, a blade unit 560, and a control unit 580. The support unit 520 and the control unit 580 of the substrate-treating apparatus 500 of FIG. 14 may have the same or similar shapes and functions as the support unit 120 and the control unit 180 of the substrate-treating apparatus 100 of FIG. 1, respectively, and thus their descriptions will be omitted or mentioned briefly for the purpose of ease and convenience in explanation. Above this, the control unit 180 may also control the blade unit 560, either. However, the substrate-treating apparatus 500 of FIG. 14 may include a plurality of optical members 552a and 552b and a reflection member 554b. For example, the optical members 552a and 552b may include a first optical member 552a and a second optical member 552b, and the reflection member 554b may be a mirror 554b provided to be opposite to the second optical member 552b.

In addition, the substrate-treating apparatus 500 may include the blade unit 560. The blade unit 560 may include a blade surface 562. The blade unit 560 may perform a process of treating the substrate 10. For example, the blade unit 560 may perform a process of removing a layer provided on the substrate 10. The process may be de-bonding process for separating the device wafer 20 from the carrier wafer 40. To perform the process, the blade unit 560 may remove the adhesive layer 60 bonding the device wafer 20 to the carrier wafer 40. For example, by using the blade surface 562 of the blade unit 560 may remove the adhesive layer 60 bonding the device wafer 20 to the carrier wafer 40. As illustrated in FIG. 16, the control unit 580 may control the support unit 520, the optical measurement unit 540, and the blade unit 560.

Referring to FIG. 15, the first optical member 552a may be disposed over the blade unit 560, and the second optical member 552b may be disposed to be spaced apart from the blade unit 560. Referring to FIGS. 17, 18, and 20, the first optical member 552a may monitor a wear condition of the blade unit 560, more specifically, the first optical member 552a may monitor a wear condition of the blade surface 562. In addition, referring to FIGS. 17, 19, and 20, the second optical member 552b and the mirror 554b may monitor a position of the blade unit 560 when the blade unit 560 approaches the substrate 10 to perform the process. For example, the second optical member 552b and the mirror 554b may monitor a position of the blade surface 562 to the X-Y plane. The second optical member 552b and the mirror 554b may monitor a moving direction of the blade surface 562 to the X-Y plane. Since the adhesive layer 60 has a thin thickness, the substrate 10 may be damaged or broken when the moving direction of the blade unit 560 is deviated from a predetermined or desired direction. Thus, the position of the blade unit 460 may be monitored by the second optical member 552b and the mirror 554b to reduce or prevent damage of the substrate 10.

Figure 21:
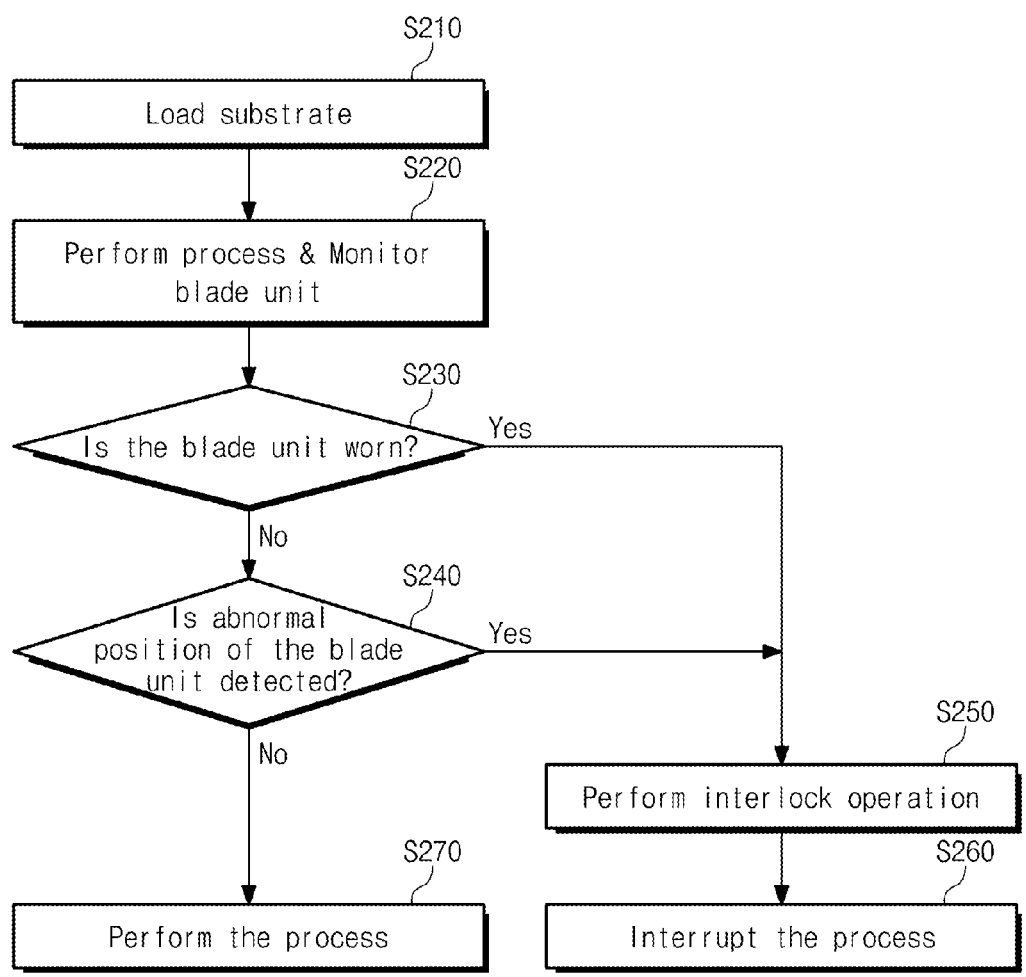
FIG. 21 is a flow chart illustrating a method of performing an interlock operation by the control unit of FIG. 14.

FIG. 21 is a flow chart illustrating a method of performing an interlock operation by the control unit 580 of FIG. 14. The substrate 10 may be loaded on the support unit 520 (S210). The substrate 10 may be a package substrate. Alternatively, the substrate 10 may be a glass substrate. Thereafter, a process may be performed on the substrate 10 and the optical measurement unit 540 may monitor the blade unit 560 (S220). At this time, the process may be the de-bonding process removing the adhesive layer 60 of the substrate 10. The control unit 580 may analyze image data transmitted from the optical measurement unit 540 to determine whether the blade unit 560 is worn or not (S230). If a wear signal of the blade unit 560 is detected, the control unit 580 may perform the interlock operation to interrupt the process (S250 and S260). If the wear signal of the blade unit 560 is not detected, the process may be continuously performed and the optical measurement unit 540 may check whether the position of the blade unit 560 is abnormal or not (S240). If an abnormal position of the blade unit 560 is detected, the control unit 580 may perform the interlock operation to interrupt the process (S250 and S260). If the abnormal position of the blade unit 560 is not detected, the process may be continuously performed.

Figure 22:
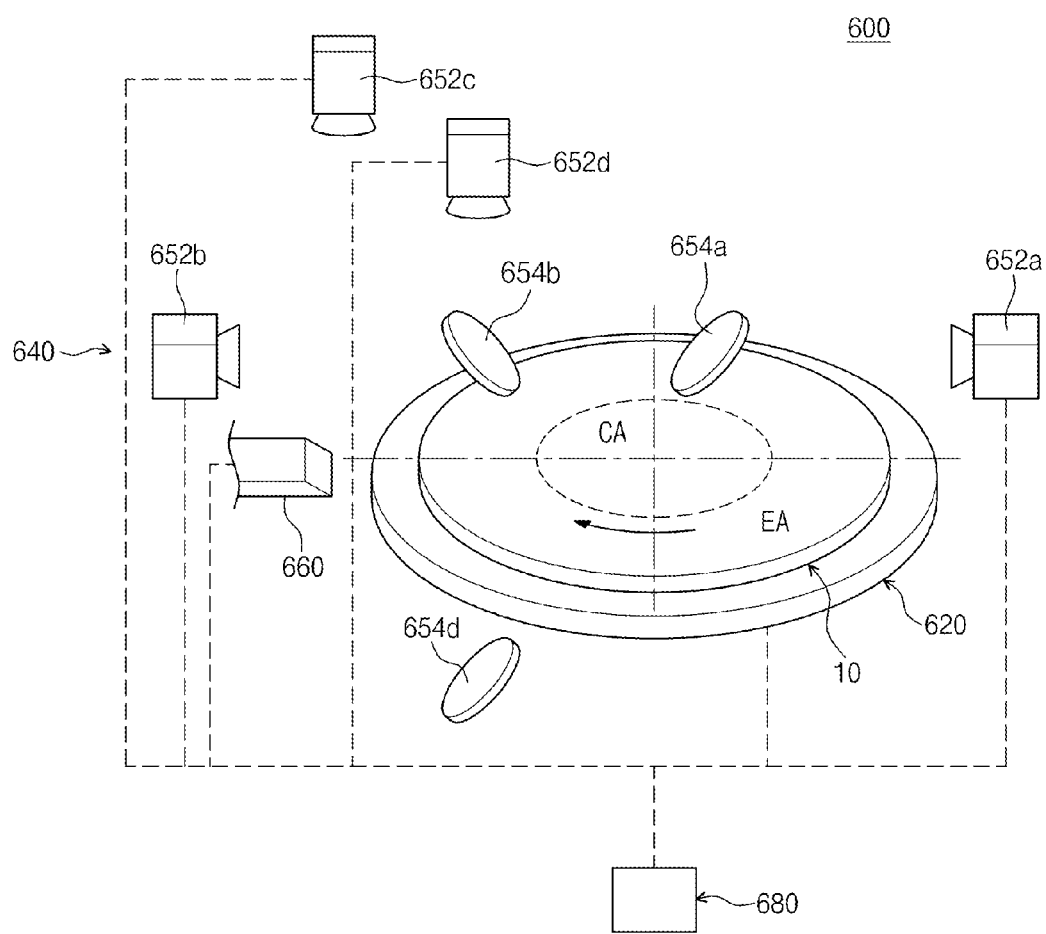
FIG. 22 is a schematic view illustrating a substrate-treating apparatus according to an example embodiment of the inventive concepts.
Figure 23:
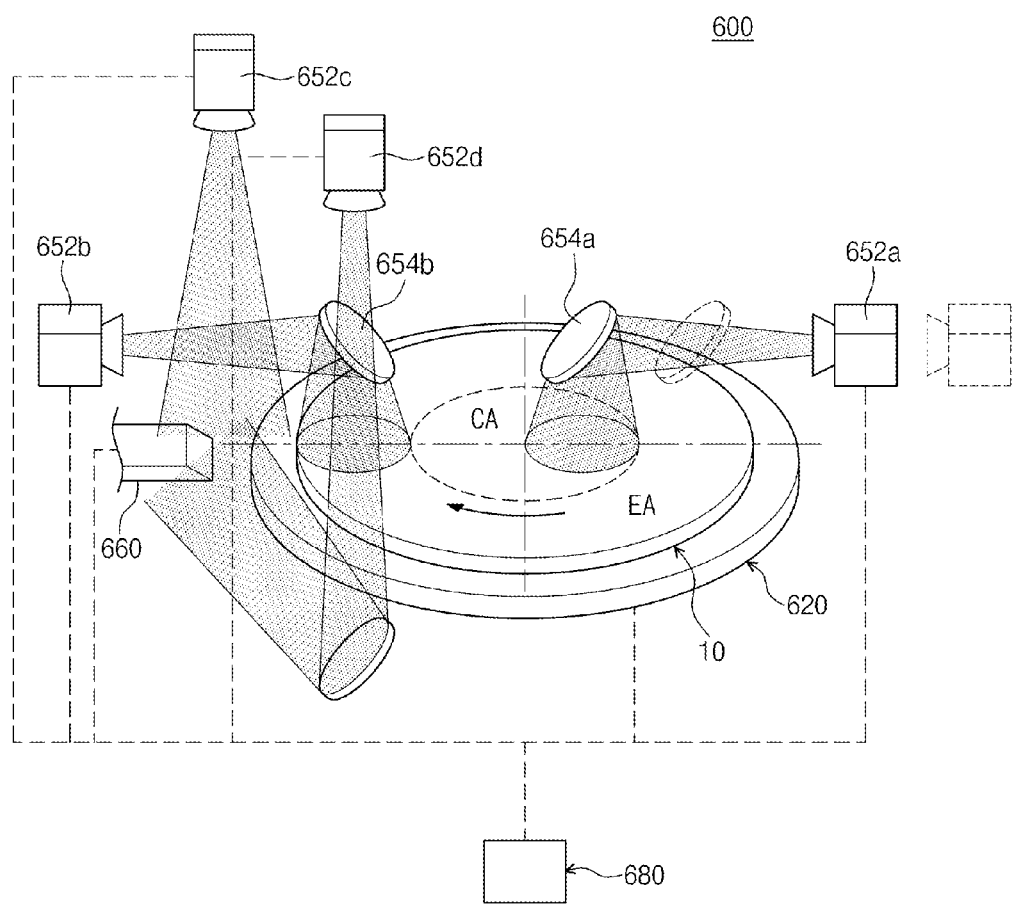
FIG. 23 is a schematic view illustrating optical measurement using the substrate-treating apparatus of FIG. 22.

FIG. 22 is a schematic view illustrating a substrate-treating apparatus 600 according to an example embodiment of the inventive concepts. FIG. 23 is a schematic view illustrating optical measurement using the substrate-treating apparatus 600 of FIG. 22.

Figure 24:
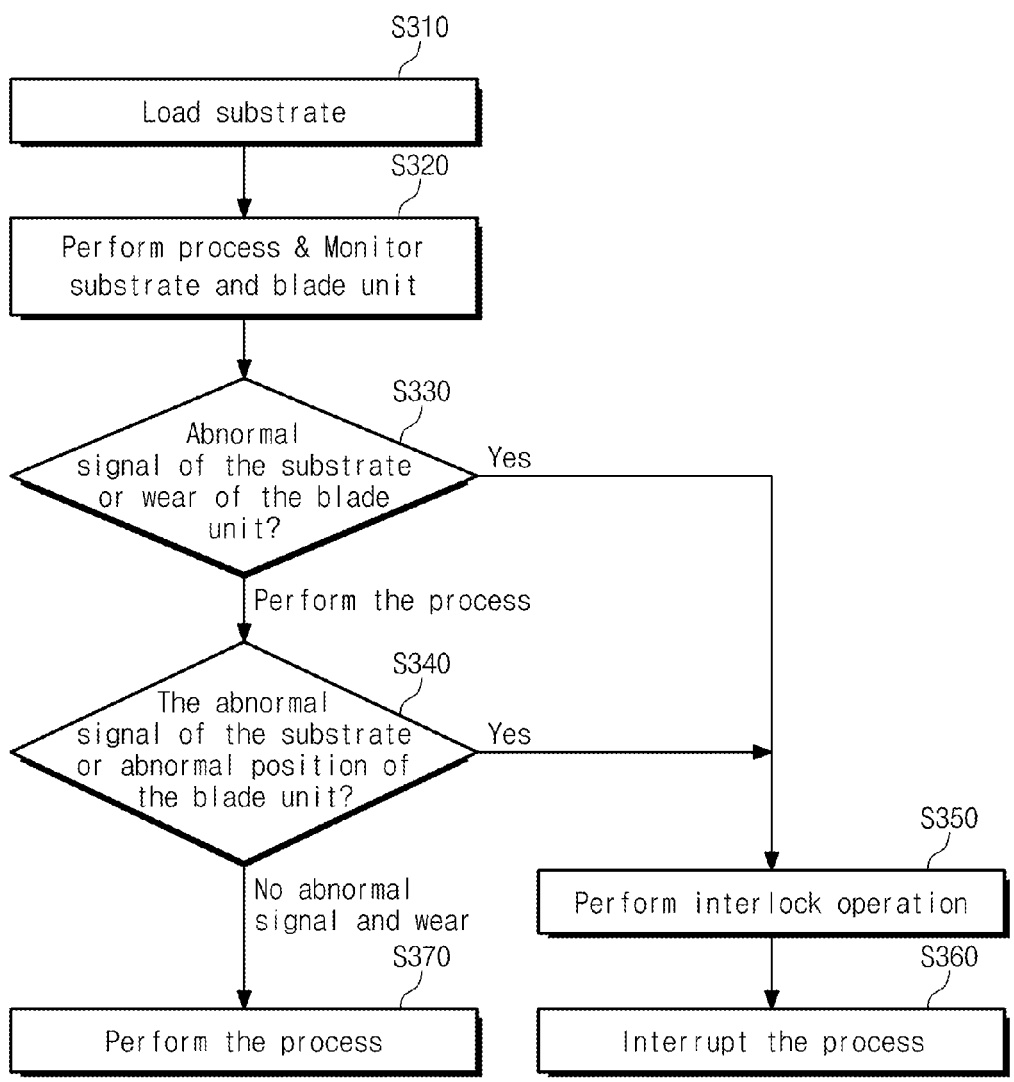
FIG. 24 is a flow chart illustrating a method of performing an interlock operation by a control unit of FIG. 22.

Referring to FIGS. 22 to 24, the substrate-treating apparatus 600 may include a support unit 620, an optical measurement unit 640, a blade unit 660, and a control unit 680. The support unit 620 of the substrate-treating apparatus 600 of FIG. 22 may have the same or similar shape and function as the support unit 120 of the substrate-treating apparatus 100 of FIG. 1. The blade unit 660 and the control unit 680 of the substrate-treating apparatus 600 of FIG. 22 may have the same or similar shapes and functions as the blade unit 560 and the control unit 580 of the substrate-treating apparatus 500 of FIG. 14. Thus, the descriptions to the support unit 620, the blade unit 660 and the control unit 680 will be omitted or mentioned briefly for the purpose of ease and convenience in explanation. However, the substrate-treating apparatus 600 may include a plurality of optical members 652a, 652b, 652c and 652d and a plurality of reflection members 654a, 654b and 654d.

The optical members 652a, 652b, 652c and 652d may include a first optical member 652a, a second optical member 652b, a third optical member 652c, and a fourth optical member 652d. The reflection members 654a, 654b and 654d may include a first mirror 654a, a second mirror 654b, and a third mirror 654d. The first mirror 654a, the second mirror 654b, and the third mirror 654d may be provided to opposite to the first optical member 652a, the second optical member 652b, and the fourth optical member 652d, respectively. The first mirror 654a and the second mirror 654b may be disposed to be opposite to each other over the substrate 10.

The first optical member 652a and the first mirror 654a may check whether the central area CA of the substrate 10 is abnormal or not, and the second optical member 652b and the second mirror 654b may check whether the edge area EA of the substrate 10 is abnormal or not. The third optical member 652c may be disposed over the blade unit 660, and the fourth optical member 652d may be disposed to be spaced apart from the blade unit 660. The third optical member 652c may monitor a wear condition of the blade unit 660, and the fourth optical member 652d and the third mirror 654d may monitor a position of the blade unit 660 when the blade unit 660 approaches the substrate 10 to perform the process. The blade unit 660 may perform a process of treating the substrate 10. In an example embodiment, the blade unit 660 may perform a process of removing a layer provided on the substrate 10.

The process may be a de-bonding process for separating the device wafer 20 from the carrier wafer 40. To perform the process, the blade unit 660 may remove the adhesive layer 60 bonding the device wafer 20 to the carrier wafer 40. Since the adhesive layer 60 has a thin thickness, the substrate 10 may be damaged or broken when a moving direction of the blade unit 660 is deviated from a predetermined or desired direction. Thus, the position of the blade unit 660 may be monitored by means of the fourth optical member 652d and the third mirror 654d to reduce or prevent damage of the substrate 10.

FIG. 24 is a flow chart illustrating a method of performing an interlock operation by a control unit 680 of FIG. 22. The substrate 10 may be loaded on the support unit 620 (S310). The substrate 10 may be a package substrate. Alternatively, the substrate 10 may be a glass substrate. Thereafter, a process may be performed on the substrate 10 and the optical measurement unit 640 may monitor the substrate 10 and the blade unit 660 (S320). At this time, the first optical member 652a and the second optical member 652b may monitor the substrate 10, and the third optical member 652c and the fourth optical member 652d may monitor the blade unit 660. The control unit 680 may analyze image data transmitted from the optical members 652a, 652b, 652c and 652d to determine whether an abnormal signal of the substrate 10 occurs or not and whether the blade unit 660 is worn or not (S330). If an abnormal signal of the substrate 10 is detected or a wear signal of the blade unit 660 is detected, the control unit 680 may perform the interlock operation to interrupt the process (S350 and S360). If the abnormal signal of the substrate 10 and the wear signal of the blade unit 660 are not detected, the process may be continuously performed, and the optical measurement unit 640 may monitor whether the abnormal signal of the substrate 10 and an abnormal position signal of the blade unit 660 are detected or not (S340). If the abnormal signal of the substrate 10 or the abnormal position signal of the blade unit 660 is detected, the control unit 680 may perform the interlock operation to interrupt the process (S350 and S360. If the abnormal signal of the substrate 10 and the abnormal position signal of the blade unit 660 are not detected, the process may be continuously performed (S370).

In the above mentioned example embodiments, the substrate-treating apparatus according to the inventive concepts optically measures the package substrate during the de-bonding process of separating the device wafer from the carrier wafer. However, example embodiments of the inventive concepts are not limited thereto. The substrate-treating apparatus according to example embodiments of the inventive concepts may optically measure and monitor the substrate during other various processes. In an example embodiment, the substrate-treating apparatus according to example embodiments of the inventive concepts may optically measure and monitor the substrate during a process of bonding the device wafer to the carrier wafer. In addition, in the aforementioned example embodiments, the blade unit may be used in the process of removing the layer included in the substrate, but example embodiments of the inventive concepts are not limited to the above mentioned function of the blade unit. The blade unit may be used in other various processes requiring a specific movement direction of the blade unit. In an example embodiment, the blade unit may be used in a substrate transfer process. Furthermore, in the above mentioned example embodiments, the package substrate including the through electrode is described as an example. However, the kind of the substrate is not limited thereto.

According to an example embodiment of the inventive concepts, the substrate-treating apparatus may optically measure the substrate and/or the blade unit to monitor defects (e.g., chippings or particles) of the substrate and the state and the position of the blade unit in real time. In addition, the substrate-treating apparatus may perform the interlock operation when the abnormal signal of the substrate or the abnormal signal of the blade unit is detected, so the apparatus may be effectively managed and a loss of the wafer may be reduced or prevented.

While the inventive concepts have been described with reference to example embodiments, it will be apparent to those skilled in the art that various changes and modifications may be made without departing from the spirits and scopes of the inventive concepts. Therefore, it should be understood that the above example embodiments are not limiting, but illustrative. Thus, the scopes of the inventive concepts are to be determined by the broadest permissible interpretation of the following claims and their equivalents, and shall not be restricted or limited by the foregoing description.

What is claimed is:

1. A substrate-treating apparatus comprising:
a support unit on which a substrate is loaded;
a blade unit at a side of the support unit and configured to remove a layer on the substrate loaded on the support unit;
an optical measurement unit configured to provide light to the substrate to obtain image data, the optical measurement unit configured to,
check whether the substrate is abnormal or not, based on the image data, and
check a wear level of the blade unit; and
a controller configured to control the support unit and the optical measurement unit, the controller configured to process the image data transmitted from the optical measurement unit,
wherein the controller includes,
an interlock configured to perform an interlock operation interrupting a process performed on the substrate if an abnormal signal is detected from the image data, and
wherein the controller is configured to perform an interlock operation interrupting operation of the blade unit, based on the wear level of the blade unit.

2. The substrate-treating apparatus of claim 1, wherein the optical measurement unit comprises:
an optical member configured to provide the light to the substrate; and
a reflection member spaced apart from the optical member, the reflection member configured to reflect the light from the optical member to adjust a measurement range of the light.

3. The substrate-treating apparatus of claim 2, wherein the controller further comprises:
an image control part configured to monitor the image data received from the optical measurement unit, wherein the image control is configured to transmit the abnormal signal to the interlock when the abnormal signal is detected.

4. The substrate-treating apparatus of claim 3, wherein the optical measurement unit further includes,
a shaft configured to support the optical member and configured to control a first direction corresponding to a height of the optical member, and
a driving part on the shaft, the driving part configured to move the optical member in a second direction and a third direction, the second direction and third direction perpendicular to the first direction.

5. The substrate-treating apparatus of claim 4, wherein the optical member includes a plurality of optical members.

6. The substrate-treating apparatus of claim 5, wherein the optical measurement unit comprises:
a first optical member and a second optical member,
wherein the first optical member is configured to check whether a central area of the substrate is abnormal or not, and
wherein the second optical member is configured to check whether an edge area of the substrate is abnormal or not.

7. The substrate-treating apparatus of claim 6, wherein the reflection member of the optical measurement unit comprises:
a first mirror opposite to the first optical member; and
a second mirror opposite to the second optical member,
wherein the first mirror is over the central area, and
wherein the second mirror is over the edge area.

8. The substrate-treating apparatus of claim 7, wherein the controller is configured to rotate the support unit to rotate the substrate when the optical measurement unit checks whether the substrate is abnormal or not.

9. The substrate-treating apparatus of claim 6,
wherein the controller is configured to control the support unit, the optical measurement unit and the blade unit.

10. The substrate-treating apparatus of claim 9, wherein the optical measurement unit further comprises: a third optical member over the blade unit, and
wherein the third optical member configured to check the wear level of blade unit.

11. The substrate-treating apparatus of claim 1, wherein the abnormal signal includes at least one of a signal corresponding to a chipping, a signal corresponding to a crack, a signal corresponding to a broken phenomenon, or a signal corresponding to a foreign substance.

12. The substrate-treating apparatus of claim 1, wherein the controller is configured to operate an alarm when the abnormal signal is detected.

13. A substrate-treating apparatus comprising:
a support unit on which a substrate is loaded, the substrate including a first carrier wafer bonded to a second device wafer;
a blade unit configured to perform a process of treating the substrate, the blade unit configured to debond the second device wafer from the first carrier wafer;
an optical measurement unit configured to provide light to check a wear level of the blade unit, the optical measurement unit configured to obtain image data corresponding to the wear level; and
a controller configured to control the support unit, the blade unit, and the optical measurement unit,
wherein the controller is configured to
process the image data received from the optical measurement unit, and
perform an interlock operation interrupting the process when the wear level of the blade unit indicates the blade unit is worn.

14. The substrate-treating apparatus of claim 13, wherein the controller is configured to perform an interlock operation interrupting the process when at least one of an abnormal signal of the substrate or an abnormal position signal of the blade unit is detected.

15. The substrate-treating apparatus of claim 14, wherein the process includes removing a layer on the substrate, and
wherein the optical measurement unit configured to detect the position of the blade unit when the blade unit approaches the layer to remove the layer.

16. The substrate-treating apparatus of claim 15, wherein the optical measurement unit comprises: a first optical member and a second optical member,
wherein the first optical member configured to check whether a central area of the substrate is abnormal or not, and
wherein the second optical member configured to check whether an edge area of the substrate is abnormal or not.

17. The substrate-treating apparatus of claim 14, wherein the abnormal signal of the substrate includes at least one of a signal corresponding to a chipping, a signal corresponding to a crack, a signal corresponding to a broken phenomenon, or a signal corresponding to a foreign substance.

18. The substrate-treating apparatus of claim 16, wherein the optical measurement unit further comprises: a third optical member and a fourth optical member,
wherein the third optical member is over the blade unit to check the wear level of the blade unit, and
wherein the fourth optical member is spaced apart from the blade unit and configured to detect the position of the blade unit.

* * * * *